United States Patent
Oshikawa et al.

(10) Patent No.: US 8,621,852 B2
(45) Date of Patent: Jan. 7, 2014

(54) DETECTOR FOR DETECTING SULFUR COMPONENTS

(75) Inventors: Katsuhiko Oshikawa, Tokyo (JP); Takamitsu Asanuma, Mishima (JP); Hiromasa Nishioka, Susono (JP); Yoshihisa Tsukamoto, Susono (JP); Hiroshi Otsuki, Susono (JP); Junichi Matsuo, Susono (JP); Kazuhiro Umemoto, Susono (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 13/322,293

(22) PCT Filed: Nov. 26, 2009

(86) PCT No.: PCT/JP2009/070278
§ 371 (c)(1),
(2), (4) Date: Nov. 23, 2011

(87) PCT Pub. No.: WO2011/064900
PCT Pub. Date: Jun. 3, 2011

(65) Prior Publication Data
US 2012/0222405 A1 Sep. 6, 2012

(51) Int. Cl.
*F01N 3/00* (2006.01)
(52) U.S. Cl.
USPC .................. 60/297; 60/276; 60/285; 60/301
(58) Field of Classification Search
USPC ............ 60/274, 276, 277, 284, 285, 297, 301
See application file for complete search history.

(56) References Cited

U.S. PATENT DOCUMENTS

| 6,263,666 | B1 * | 7/2001 | Kubo et al. ..................... 60/277 |
| 6,679,050 | B1 * | 1/2004 | Takahashi et al. .............. 60/285 |
| 7,134,274 | B2 * | 11/2006 | Asanuma ......................... 60/295 |
| 8,151,555 | B2 * | 4/2012 | Niimi et al. ..................... 60/286 |
| 8,307,639 | B2 * | 11/2012 | Nishioka et al. ................ 60/301 |
| 8,375,706 | B2 * | 2/2013 | Iida et al. ........................ 60/295 |

FOREIGN PATENT DOCUMENTS

| EP | 2 058 647 A1 | 5/2009 |
| JP | A-2008-175623 | 7/2008 |
| JP | A-2008-286061 | 11/2008 |
| JP | A-2009-030459 | 2/2009 |
| JP | A-2009-138525 | 6/2009 |

OTHER PUBLICATIONS

International Search Report in International Application No. PCT/JP2009/070278; dated Jan. 19,2010 (with English-language translation).

* cited by examiner

*Primary Examiner* — Binh Q Tran
(74) *Attorney, Agent, or Firm* — Oliff & Berridge, PLC

(57) ABSTRACT

The present detector for detecting sulfur components includes a storage portion for storing $SO_x$ and $NO_x$ in the exhaust gas passing through an exhaust passage, in which the more an amount of stored $SO_x$ increases, the more an amount of stored $NO_x$ decreases, and which does not release $SO_x$ but release $NO_x$ at a set temperature, and a temperature sensor, estimates the amount of stored $SO_x$ on the basis of a relationship between, after the storage portion becomes the set temperature by heating, a heating pattern of the storage portion and temperature change of the storage portion measured by the temperature sensor, and detects an integrated amount of $SO_x$ passing through the exhaust passage during a given period or an value on the basis of the integrated amount.

9 Claims, 2 Drawing Sheets

EXHAUST GAS FLOW

EXHAUST GAS FLOW →

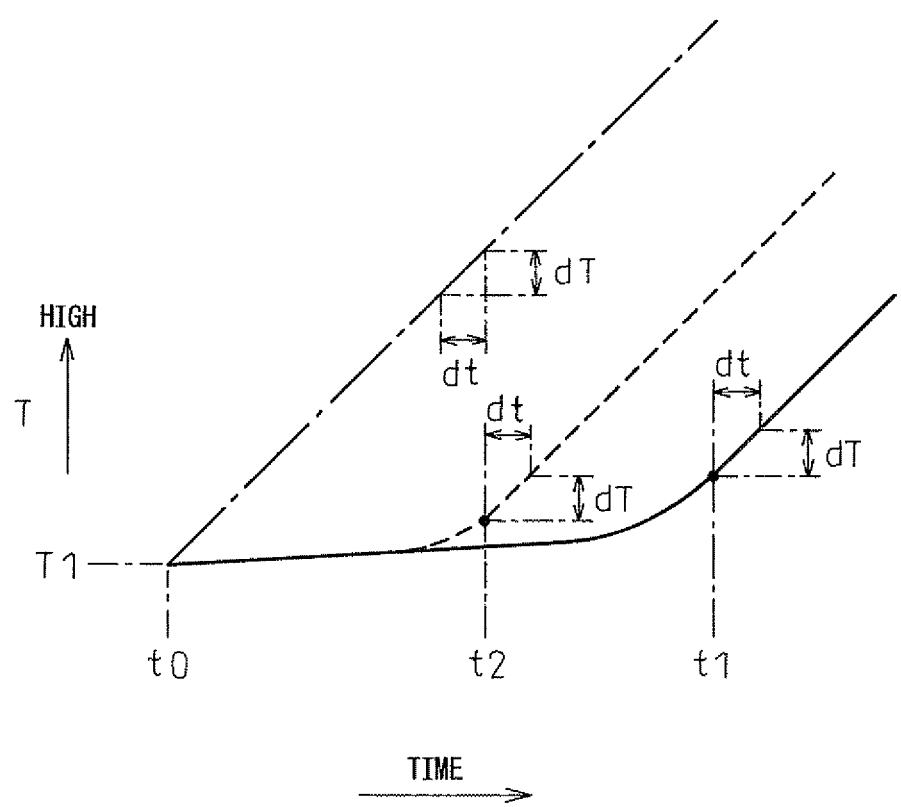

DETECTOR FOR DETECTING SULFUR COMPONENTS

TECHNICAL FIELD

The present invention relates to a detector for detecting sulfur components.

BACKGROUND ART

A $SO_x$ concentration sensor for detecting a $SO_x$ concentration in exhaust gas is known. A normal $SO_x$ concentration sensor measures electromotive force produced when $SO_x$ changes into sulfuric acid ion within a solid electrolyte, in order to detect a $SO_x$ concentration in the exhaust gas. However, it is difficult for this $SO_x$ concentration sensor to detect an accurate $SO_x$ concentration when the $SO_x$ concentration in the exhaust gas is low.

A proposed detector for detecting sulfur components cannot detect an instantaneous $SO_x$ concentration but can detect an integrated amount of $SO_x$ passing through the exhaust passage during a given period (for example, refer to Japanese Unexamined Patent Publication No. 2008-175623).

The detector for detecting sulfur components comprises a $SO_x$ storage portion for storing $SO_x$ contained in the exhaust gas, measures a property such as electric resistance, volume, heat capacity or the like of the $SO_x$ storage portion, which changes according to the increase in an amount of $SO_x$ stored in the $SO_x$ storage portion, and detects an integrated amount of $SO_x$ passing through the exhaust passage during a given period on the basis of the measured property.

DISCLOSURE OF THE INVENTION

Since it is difficult to accurately measure a change in electric resistance, volume, heat capacity or the like, the above-mentioned detector may be not able to accurately detect an integrated amount of $SO_x$ passing through the exhaust passage during a given period.

Accordingly, an object of the present invention is to provide a detector for detecting sulfur components, which can accurately detect an integrated amount of $SO_x$ passing through the exhaust passage in a given period or a value on the basis of the integrated amount.

A first detector for detecting sulfur components of the present invention is provided. The first detector comprises a storage portion for storing $SO_x$ and $NO_x$ in the exhaust gas passing through an exhaust passage, in which the more an amount of stored $SO_x$ increases, the more an amount of stored $NO_x$ decreases, and which does not release $SO_x$ but release $NO_x$ at a set temperature, and a temperature sensor, estimates the amount of stored $SO_x$ on the basis of a relationship between, after the storage portion becomes the set temperature by heating, a heating pattern of the storage portion and temperature change of the storage portion measured by the temperature sensor, and defects an integrated amount of $SO_x$ passing through the exhaust passage during a given period or an value on the basis of the integrated amount.

A second detector for detecting sulfur components of the present invention is provided as the first detector characterized in that the heating pattern being set so as to elevate the temperature of the storage portion when $NO_x$ is not stored by a predetermined temperature per unit time, so that the temperature of the storage portion while $NO_x$ is stored elevates by a temperature lower than the predetermined temperature per unit time by the heating pattern, all of the $NO_x$ released from the storage portion being estimated on the basis that $NO_x$ is released during a period in which the temperature of the storage portion elevates by the temperature lower than the predetermined temperature per unit time, and the amount of stored $SO_x$ being estimated on the basis of all of the released $NO_x$.

A third detector for detecting sulfur components of the present invention is provided as the first or second detector characterized in that the storage portion being elevated to the set temperature and over by heating of the exhaust gas, and the amount of stored $SO_x$ being estimated on the basis of the heating pattern by the exhaust gas.

A fourth detector for detecting sulfur components of the present invention is provided as the first or second detector characterized in that an electric heater being provided to heat the storage portion, the storage portion being elevated to the set temperature and over by heating of the electric heater, and the amount of stored $SO_x$ being estimated on the basis of the heating pattern by the electric heater.

A fifth detector for detecting sulfur components of the present invention is provided as the first, second, third, or fourth detector characterized in that when the oxygen concentration in the exhaust gas being lowered, the storage portion releasing the stored $NO_x$ and reducing the released $NO_x$ by using of reduction materials in the exhaust gas, so that the temperature of the storage portion elevates by heat produced in the reduction of $NO_x$, if necessary, the amount of stored $SO_x$ being estimated on the basis of an increase value of temperature of the storage portion measured by the temperature sensor after the oxygen concentration in the exhaust gas is lowered, and the integrated amount of $SO_x$ passing through the exhaust passage during the given period or the value on the basis of the integrated amount being detected.

According to the first detector for detecting sulfur components of the present invention, the storage portion in which the more an amount of stored $SO_x$ increases, the more an amount of stored $NO_x$ decreases, does not release $SO_x$ but release $NO_x$ at the set temperature. An amount of $NO_x$ stored in the storage portion can be estimated on the basis of a relationship between, after the storage portion becomes the set temperature by heating, a heating pattern of the storage portion and temperature change of the storage portion measured by the temperature sensor. Therefore, because the larger an amount of stored $NO_x$ is, the smaller an amount of $SO_x$ stored in the storage portion is, an amount of stored $SO_x$ can be estimated. A given rate of an amount of $SO_x$ passing through the exhaust passage is stored in the storage portion of the detector. Therefore, an integrated amount of $SO_x$ passing through the exhaust passage during the given period or a value on the basis of the integrated amount can be accurately detected on the basis of the amount of $SO_x$ stored in the storage portion.

According to the second detector for detecting sulfur components of the present invention, in the first detector, the heating pattern of the storage portion is set so as to elevate the temperature of the storage portion when $NO_x$ is not stored by a predetermined temperature per unit time, so that the temperature of the storage portion while $NO_x$ is stored in the storage portion elevates by a temperature lower than the predetermined temperature per unit time by the heating pattern. All amount of $NO_x$ released from the storage portion is estimated on the basis that $NO_x$ is released during a period in which the temperature of the storage portion elevates by the temperature lower than the predetermined temperature per unit time and thus the amount of $SO_x$ stored in the storage portion can be estimated on the basis of the all amount of released $NO_x$. Therefore, an integrated amount of $SO_x$ passing through the exhaust passage during the given period or a value on the basis of the integrated amount can be accurately detected.

According to the third detector for detecting sulfur components of the present invention, in the first or second detector, the storage portion is elevated to the set temperature and over by heating of the exhaust gas, and the amount of $SO_x$ stored in the storage portion is estimated on the basis of the heating pattern by the exhaust gas. Thus, an integrated amount of $SO_x$ passing through the exhaust passage during the given period or a value on the basis of the integrated amount can be accurately detected.

According to the fourth detector for detecting sulfur components of the present invention, in the first or second detector, an electric heater is provided to heat the storage portion, the storage portion is elevated to the set temperature and over by heating of the electric heater, and the amount of $SO_x$ stored in the storage portion is estimated on the basis of the heating pattern by the electric heater. Thus, an integrated amount of $SO_x$ passing through the exhaust passage during the given period or a value on the basis of the integrated amount can be accurately detected.

According to the fifth detector for detecting sulfur components of the present invention, in the first, second, third, or fourth detector, when the oxygen concentration in the exhaust gas is lowered, the storage portion releases the stored $NO_x$ and reduces the released $NO_x$ by using of reduction materials in the exhaust gas, so that the temperature of the storage portion elevates by heat produced in the reduction of $NO_x$. If necessary, the amount of $NO_x$ stored in the storage portion can be estimated on the basis of an increase value of temperature of the storage portion measured by the temperature sensor after the oxygen concentration in the exhaust gas is lowered. Therefore, because the larger an amount of stored $NO_x$ is, the smaller an amount of $SO_x$ stored in the storage portion, an amount of stored $SO_x$ can be estimated. A given rate of an amount of $SO_K$ passing through the exhaust passage is stored in the storage portion of the detector. Therefore, an integrated amount of $SO_x$ passing through the exhaust passage during the given period or a value on the basis of the integrated amount can be accurately detected on the basis of the amount of $SO_x$ stored in the storage portion.

BRIEF DESCRIPTION OF THE DRAWINGS

FIG. 3 is a graph showing change of the temperature of the detector for detecting sulfur components of FIG. 2.

BEST MODE FOR CARRYING OUT THE INVENTION

Figure 1:
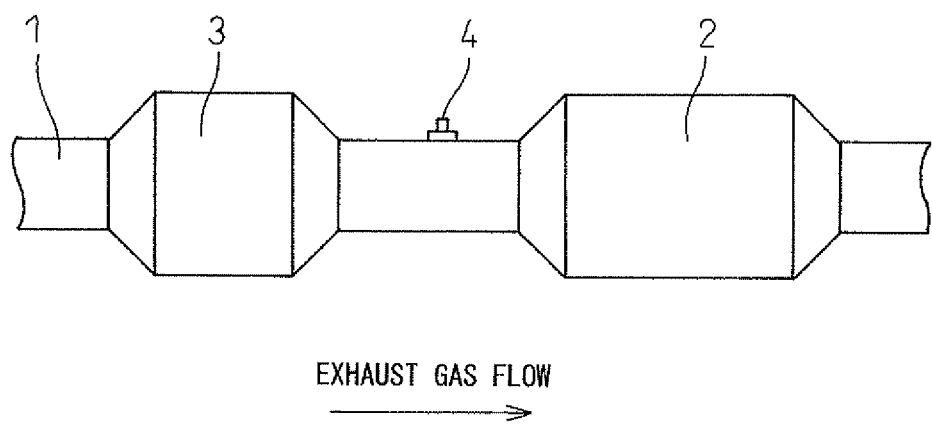
FIG. 1 is a schematic view showing an engine exhaust system in which a detector for detecting sulfur components according to the present invention is arranged.

FIG. 1 is a schematic view showing an engine exhaust system in which a detector for detecting sulfur components according to the present invention is arranged. In FIG. 1, reference numeral 1 is an exhaust passage of an internal combustion engine. The engine performs lean combustion such as in a diesel engine or a direct fuel injection-type spark-ignition engine. The exhaust gas of such an engine includes a relatively large amount of $NO_x$ so that a $NO_x$ catalyst device 2 for purifying $NO_x$ is arranged in the exhaust passage 1.

The $NO_x$ catalyst device 2 carries a $NO_x$ storage material and a noble metal catalyst such as platinum Pt. The $NO_x$ storage material is at least one element selected from for example potassium K, sodium Na, lithium Li, cesium Cs, or another alkali metal, barium Ba, calcium Ca, or another alkali earth metal, and lanthanum La, yttrium Y, or another rare earth.

The $NO_x$ catalyst device 2 satisfactorily stores $NO_x$ in the exhaust gas so as to absorb $NO_x$ as nitrate or so as to adsorb $NO_x$ as $NO_2$ when the air-fuel ratio of the exhaust gas is lean, that is, when the oxygen concentration of the exhaust gas is high. However, the $NO_x$ catalyst device cannot store $NO_x$ without limitation. Accordingly, before the $NO_x$ catalyst device can not almost store further $NO_x$ because an amount of $NO_x$ stored in the $NO_x$ catalyst device almost reaches the largest amount of $NO_x$ that can be stored therein, the air-fuel ratio of the exhaust gas is changed to a stoichiometric air-fuel ratio or a rich air-fuel ratio as the regeneration treatment, namely, the concentration of oxygen of the exhaust gas is lowered. Therefore, the stored $NO_x$ is separated, namely, the absorbed $NO_x$ is released or the adsorbed $NO_2$ is disconnected, and thereafter the separated $NO_x$ is reduced and purified to $N_2$ by reducing materials in the exhaust gas.

Once the $NO_x$ catalyst device 2 stores $SO_x$ in the exhaust gas as sulfate, sulfate is more stable than nitrate so that the stored $SO_x$ cannot be released by the regeneration treatment and an amount of $NO_x$ that can be stored drops (sulfur contamination). Therefore, an S trap device 3 which can store $SO_x$ in the exhaust gas is arranged upstream of the $NO_x$ catalyst device 2 in the exhaust passage 1 to restrain the sulfur contamination of the $NO_x$ catalyst device 2.

The detector for detecting sulfur components 4 according to the present invention is arranged, for example, between the S trap device 3 and the $NO_x$ catalyst device 2, and detects an integrated amount of $SO_x$ passing through the S trap device 3. When the integrated amount of $SO_x$ reaches a set value, it can be determined that it is time to exchange the S trap device 3 for a new one.

Figure 2:
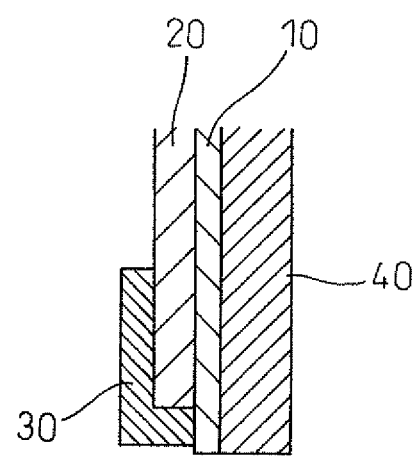
FIG. 2 is a schematic sectional view showing an embodiment of the detector for detecting sulfur components according to the present invention.

FIG. 2 is a schematic sectional view showing an embodiment of the detector for detecting sulfur components 4 according to the present invention. In FIG. 2, reference numeral 10 is a base plate. Reference numeral 20 is a temperature sensor 42 such as a thermocouple arranged on the base plate 10. Reference numeral 30 is a storage portion for $NO_x$ and $SO_x$ arranged so as to cover the temperature sensitive portion of the temperature sensor 20. Reference numeral 40 is an electric heater arranged on the base plate 10 opposite the temperature sensor 20. The storage portion 30 stores $NO_x$ and $SO_x$ in the exhaust gas and, for example, can be formed to apply the above-mentioned $NO_x$ storage material and a noble metal catalyst such as platinum Pt on the temperature sensitive portion of the temperature sensor 20.

As mentioned above, the storage portion for $NO_x$ and $SO_x$ 30 constructed like this absorb $NO_x$ in the exhaust gas as nitrate and absorb $SO_x$ in the exhaust gas as sulfate. In the storage portion for $NO_x$ and $SO_x$ 30, a total of an amount of $NO_x$ that can be stored and an amount of $SO_x$ that can be stored is constant. Sulfate is more stable than nitrate so that in the storage portion for $NO_x$ and $SO_x$ 30, an amount of stored $SO_x$ keeps on increasing, and the more an amount of stored $SO_x$ increases, the more an amount of $NO_x$ that can be stored decreases, Accordingly, if an amount of stored $NO_x$ when a current upper limit amount of $NO_x$ is stored is detected, a current amount of stored $SO_x$ can be estimated because the smaller the amount of stored $NO_x$ is, the larger an amount of stored $SO_x$ is. Since a give rate of an amount of $SO_x$ passing through the exhaust passage 1 at the position of the detector for detecting sulfur components 4 is stored in the storage portion for $NO_x$ and $SO_x$ 30 of the detector 4, an integrated amount of $SO_x$ passing through the exhaust passage 1 at the position of the detector for detecting sulfur components 4 during a given period between the initial engine start time and the current time can be accurately detected on the basis of the current amount of stored $SO_x$.

On the other hand, as a value on the basis of the integrated amount of $SO_x$, an average value of each $SO_x$ concentration in the exhaust gas passing through the exhaust passage 1 at the position of the detector for detecting sulfur components during the given period can be also detected or an average value of each amount of $SO_x$ passing through the exhaust passage 1 at the position of the detector for detecting sulfur components during the given period can be also detected.

As explained below, the detector for detecting sulfur components 4 of the present embodiment estimates a current amount of stored $SO_x$ on the basis of output of the temperature sensor 20 with operating the electric heater 40 by an electronic control unit.

When the temperature of the storage portion for $NO_x$ and $SO_x$ 30 using the $NO_x$ storage material becomes, for example, a set temperature (T1) (for example 500 degrees C.), it does not release $SO_x$ but release $NO_x$ without lowering the oxygen concentration in the exhaust gas.

When a current amount of $SO_x$ stored in the storage portion for $NO_x$ and $SO_x$ 30 of the detector for detecting sulfur components 4 is estimated, first, it is confirmed if the temperature of the storage portion for $NO_x$ and $SO_x$ 30 is a temperature (for example 300 degrees C.) which is sufficiently lower than the set temperature (T1) for some time, the $NO_x$ storage material and the noble metal catalyst of the storage portion for $NO_x$ and $SO_x$ 30 sufficiently activate and the lean-burn of which exhaust gas includes a relatively large amount of $NO_x$ is carried out. Once these are confirmed, the storage portion for $NO_x$ and $SO_x$ 30 stores a current upper limit amount of $NO_x$.

Next, as shown in FIG. 3, heat is generated by the electric heater 40 with turning on the electricity to heat the storage portion for $NO_x$ and $SO_x$ 30, and thus the temperature of the storage portion for $NO_x$ and $SO_x$ 30 is made the set temperature (T1). From this time (t0), the electricity of the electric heater 40 is controlled such that the storage portion for $NO_x$ and $SO_x$ 30 is heated by a heating pattern in which the temperature of the storage portion for $NO_x$ and $SO_x$ 30 when $NO_x$ is not completely stored is elevated by a predetermined temperature (dT) per unit time (dt) as shown by the chain line.

The heating pattern actually makes the storage portion for $NO_x$ and $SO_x$ 30 release the stored $NO_x$ from the time (t0) when the temperature of the storage portion for $NO_x$ and $SO_x$ 30 becomes the set temperature (T1). For example, in case that barium Ba is used as the $NO_x$ storage material, an endothermic reaction such as $Ba(NO_3)_2 \rightarrow BaO + 2NO + 3/2O_2 - 619$ kJ/mol occurs.

Thus, while $NO_x$ is released, heat for releasing $NO_x$ is required so that the temperature of the storage portion for $NO_x$ and $SO_x$ 30 is elevated by a temperature which is lower than the predetermined temperature (dT) per the unit time (dt) as shown by the solid line. After all amount of $NO_x$ has been released at time (t1), the temperature of the storage portion for $NO_x$ and $SO_x$ 30 is elevated by the predetermined temperature (dt) per the unit time (dt) as shown by the solid line.

The higher the predetermined temperature (dT) by the heating pattern is, the larger an amount of $NO_x$ released from the storage portion for $NO_x$ and $SO_x$ 30 per the unit time becomes. Because $NO_x$ is released in a period from the time (t0) to the time (t1), all amount of released $NO_x$, this is, an amount of $NO_x$ stored in the storage portion for $NO_x$ and $SO_x$ 30 at the time (t0) can be estimated on the basis of the heating pattern and the period from the time (t0) to the time (t1). Therefore, a current amount of $SO_x$ stored in the storage portion for $NO_x$ and $SO_x$ 30 can be estimated.

Once the amount of $SO_x$ stored in the storage portion for $NO_x$ and $SO_x$ 30 further increases so that an amount of $NO_x$ that can be stored further decrease, by the same heating pattern to elevate the temperature of the storage portion for $NO_x$ and $SO_x$ 30 when $NO_x$ is not completely stored by the predetermined temperature (dT) per the unit time (dt), all the amount of $NO_x$ has been released before the time (t1) so that the temperature of the storage portion for $NO_x$ and $SO_x$ 30 is elevated by the predetermined temperature (dT) per the unit time (dt) at time (t2) before the time (t1).

All of the released $NO_x$ can be simply calculated by multiplying an amount of $NO_x$ released per the unit time every the predetermined temperature (dT) by the heating pattern and the releasing period (from (t0) to (t1) or from (t0) to (t2)). However, strictly speaking, the amount of $NO_x$ released per the unit time is not determined on the basis of only the predetermined temperature (dT). The higher the temperature of the storage portion for $NO_x$ and $SO_x$ 30 at each time is, the larger the amount of $NO_x$ released per the unit time becomes. The larger the amount of $NO_x$ stored in the storage portion for $NO_x$ and $SO_x$ 30 at each time is, the larger the amount of $NO_x$ released per the unit time becomes. Accordingly, taking account of these, all of the released $NO_x$ calculated as mentioned above is preferably corrected.

A difference between a quantity of heat supplied to the storage portion for $NO_x$ and $SO_x$ 30 between the time (t0) and the time (t1) (or the time (t2)) and a quantity of heat required to make the temperature of the storage portion for $NO_x$ and $SO_x$ 30 from the set temperature (T1) to the temperature at the time (t1) (or the time (t2)) is a quantity of heat used to release all of the $NO_x$ from the storage portion for $NO_x$ and $SO_x$ 30. Because the larger this difference quantity of heat is, the larger the amount of released $NO_x$ is, the amount of $NO_x$ stored in the storage portion for $NO_x$ and $SO_x$ 30 at the time (t0) may be estimated on the basis of this difference quantity of heat. Strictly speaking, a quantity of heat released from the storage portion for $NO_x$ and $SO_x$ 30 is generated at each time on the basis of a difference between the temperature of the storage portion for $NO_x$ and $SO_x$ 30 at each time and the surrounding temperature so that the quantity of heat released from the storage portion for $NO_x$ and $SO_x$ is preferably subtracted from the quantity of heat supplied to the storage portion for $NO_x$ and $SO_x$ 30 at each time.

The heating pattern is not limited to one making the temperature of the storage portion for $NO_x$ and $SO_x$ when $NO_x$ is completely stored elevate by the predetermined temperature (dT) per unit time (dt), and may be one making the temperature elevated per unit time vary in two stages or multi-stages. In any case, if the heating pattern is clear, all of the released $NO_x$ can be estimated on the basis of the heating pattern and the period while $NO_x$ is released (from the time at which the temperature of the storage portion for $NO_x$ and $SO_x$ 30 becomes the set temperature (T1) to the time when the temperature of the storage portion for $NO_x$ and $SO_x$ 30 elevated per unit time corresponds to the predetermined one indicating the complete release of $NO_x$), for example, by using of the above mentioned idea of the difference between quantities of heat, and thus the current amount of $SO_x$ stored in the storage portion for $NO_x$ and $SO_x$ 30 can be estimated.

In the detector for detecting sulfur components 4 of the present embodiment, the electric heater 40 heats the storage portion for $NO_x$ and $SO_x$ 30. The present invention is not limited by the storage portion heated by the electric heater. For example, when a specific steady engine operation in which the temperature of the exhaust gas becomes more than the set temperature (T1) is carried out, the current amount of $SO_x$ stored in the storage portion for $NO_x$ and $SO_x$ 30 of the detector for detecting sulfur components 4 can be estimated.

In the specific steady engine operation, the engine speed and the engine load (the high engine load) are constant, the flow rate of the exhaust gas is constant, and the temperature of the exhaust gas more than the set temperature (T1) is also constant. At this time, the temperature of the storage portion for $NO_x$ and $SO_x$ 30 becomes the set temperature (T1) by heating of the exhaust gas and a heating pattern thereafter of the storage portion for $NO_x$ and $SO_x$ 30 by the exhaust gas can be predetermined by way of experiment or the like. Accordingly, all of the released $NO_x$ can be estimated on the basis of the heating pattern and the period while $NO_x$ is released (from the time at which the temperature of the storage portion for $NO_x$ and $SO_x$ 30 becomes the set temperature (T1) to the time when the temperature of the storage portion for $NO_x$ and $SO_x$ 30 elevated per unit time corresponds to the predetermined one indicating to the complete release of $NO_x$), for example, by using of the above mentioned idea of the difference between quantities of heat, and thus the current amount of $SO_x$ stored in the storage portion for $NO_x$ and $SO_x$ 30 can be estimated.

Incidentally, the detector for detecting sulfur components 4 of the present embodiment releases the stored $NO_x$ and reduces the released $NO_x$ by the reduction materials in the exhaust gas, similarly with the $NO_x$ catalyst device 2 when the oxygen concentration in the exhaust gas is lowered. The heat generated by the reduction of $NO_x$ elevates the temperature of the storage portion of $NO_x$ and $SO_x$ 30. Therefore, if an increase value of temperature of the storage portion 30 when all of the $NO_x$ is released and reduced after the concentration of oxygen in the exhaust gas is lowered, i.e., the difference temperature between the temperature of the storage portion for $NO_x$ and $SO_x$ 30 when the concentration of oxygen in the exhaust gas is lowered and a peak temperature of the storage portion for $NO_x$ and $SO_x$ 30 thereafter, is detected by the temperature sensor 20, the amount of $NO_x$ stored in the storage portion for $NO_x$ and $SO_x$ 30 can be estimated because the higher the increase value of temperature is, the more the amount of reduced $NO_x$ released from the storage portion for $NO_x$ and $SO_x$ 30 is. Accordingly, the current amount of $SO_x$ stored in the storage portion for $NO_x$ and $SO_x$ 30 can be estimated.

For example, in the regeneration treatment of the $NO_x$ catalyst device 2, as mentioned above, the air-fuel ratio of the exhaust gas is made rich to lower the concentration of oxygen. At this time, if the temperature of the storage portion of $NO_x$ and $SO_x$ 30 is observed, the current amount of $SO_x$ stored in the storage portion for $NO_x$ and $SO_x$ 30 can be estimated without heating of the storage portion for $NO_x$ and $SO_x$ 30.

When the concentration of oxygen in the exhaust gas is lowered, a part of oxygen included in the exhaust gas generates heat with reducing the reduction material in the exhaust gas at the storage portion for $NO_x$ and $SO_x$ 30. Accordingly, the temperature of the storage portion 30 elevated by this generated heat is preferably subtracted from the measured elevated temperature of the storage portion for $NO_x$ and $SO_x$ 30. For that purpose, it is preferable that an amount of oxygen included in the exhaust gas when the concentration of oxygen in the exhaust gas is lowered is estimated or measured and the temperature subtracted from the measured elevated temperature for $NO_x$ and $SO_x$ 30 is preset on the basis that a specified rate of the predetermined amount of oxygen generates heat with reducing the reduction material in the exhaust gas at the storage portion for $NO_x$ and $SO_x$ 30.

LIST OF REFERENCE NUMERALS

1: exhaust passage
2: $NO_x$ catalyst device
3: S trap device
4: detector for detecting sulfur components
20: temperature sensor
30: storage portion for $NO_x$ and $SO_x$
40: electric heater

The invention claimed is:

1. A detector for detecting sulfur components comprising:
a storage portion for storing $SO_x$ and $NO_x$ in the exhaust gas passing through an exhaust passage, in which the more an amount of stored $SO_x$ increases, the more an amount of stored $NO_x$ decreases, and which does not release $SO_x$ but releases $NO_x$ at a set temperature; and
a temperature sensor;
wherein:
the detector:
estimates said amount of stored $SO_x$ on the basis of a relationship between (after said storage portion becomes said set temperature by heating) a heating pattern of said storage portion and temperature chance of said storage portion measured by said temperature sensor, and
detects an integrated amount of $SO_x$ passing through said exhaust passage during a given period or a value on the basis of said integrated amount;
said heating pattern is set so as to elevate the temperature of said storage portion when $NO_x$ is not stored by a predetermined temperature per unit time;
the temperature of said storage portion while $NO_x$ is stored elevates by a temperature lower than said predetermined temperature per unit time by said heating pattern;
all $NO_x$ released from said storage portion being estimated on the basis that $NO_x$ is released during a period in which the temperature of said storage portion elevates by the temperature lower than said predetermined temperature per unit time; and
said amount of stored $SO_x$ being estimated on the basis of all of the released $NO_x$.

2. A detector for detecting sulfur components comprising:
a storage portion for storing $SO_x$ and $NO_x$ in the exhaust gas passing through an exhaust passage, in which the more an amount of stored $SO_x$ increases, the more an amount of stored $NO_x$ decreases, and which does not release $SO_x$ but release $NO_x$ at a set temperature, and
a temperature sensor:
wherein:
the detector:
estimates said amount of stored $SO_x$ on the basis of a relationship between (after said storage portion becomes said set temperature by heating) a heating pattern of said storage portion and temperature change of said storage portion measured by said temperature sensor, and
detects an integrated amount of $SO_x$ passing through said exhaust passage during a given period or an value on the basis of said integrated amount, and
when the oxygen concentration in the exhaust gas is lowered, said storage portion releases the stored $NO_x$ and reduces the released $NO_x$ by using reduction materials in the exhaust gas, so that the temperature of said storage portion elevates due to heat produced in the reduction of $NO_x$, if necessary, said amount of stored $SO_x$ is estimated on the basis of an increase value of temperature of said storage portion measured by said temperature sensor after the oxygen concentration in the exhaust gas is lowered, and the integrated amount of $SO_x$ passes through the exhaust passage during the given period or the value on the basis of said integrated amount being detected.

3. A detector for detecting sulfur components according to claim 1 wherein said storage portion being elevated to said set temperature and over by heating of the exhaust gas, and said amount of stored $SO_x$ being estimated on the basis of said heating pattern by the exhaust gas.

4. A detector for detecting sulfur components according to claim 1 wherein an electric heater being provided to heat said storage portion, said storage portion being elevated to said set temperature and over by heating of said electric heater, and said amount of stored $SO_x$ being estimated on the basis of said heating pattern by said electric heater.

5. A detector for detecting sulfur components according to claim 1 wherein when the oxygen concentration in the exhaust gas being lowered, said storage portion releasing the stored $NO_x$ and reducing the released $NO_x$ by using of reduction materials in the exhaust gas, so that the temperature of said storage portion elevates by heat produced in the reduction of $NO_x$, if necessary, said amount of stored $SO_x$ being estimated on the basis of an increase value of temperature of said storage portion measured by said temperature sensor after the oxygen concentration in the exhaust gas is lowered, and the integrated amount of $SO_x$ passing through the exhaust passage during the given period or the value on the basis of said integrated amount being detected.

6. A detector for detecting sulfur components according to claim 2, wherein said storage portion being elevated to said set temperature and over by heating of the exhaust gas, and said amount of stored $SO_x$ being estimated on the basis of said heating pattern by the exhaust gas, and when the oxygen concentration in the exhaust gas being lowered, said storage portion releasing the stored $NO_x$ and reducing the released $NO_x$ by using of reduction materials in the exhaust gas, so that the temperature of said storage portion elevates by heat produced in the reduction of $NO_x$, if necessary, said amount of stored $SO_x$ being estimated on the basis of an increase value of temperature of said storage portion measured by said temperature sensor after the oxygen concentration in the exhaust gas is lowered, and the integrated amount of $SO_x$ passing through the exhaust passage during the given period or the value on the basis of said integrated amount being detected.

7. A detector for detecting sulfur components according to claim 3 wherein when the oxygen concentration in the exhaust gas being lowered, said storage portion releasing the stored $NO_x$ and reducing the released $NO_x$ by using of reduction materials in the exhaust gas, so that the temperature of said storage portion elevates by heat produced in the reduction of $NO_x$, if necessary, said amount of stored $SO_x$ being estimated on the basis of an increase value of temperature of said storage portion measured by said temperature sensor after the oxygen concentration in the exhaust gas is lowered, and the integrated amount of $SO_x$ passing through the exhaust passage during the given period or the value on the basis of said integrated amount being detected.

8. A detector for detecting sulfur components according to claim 2, wherein an electric heater being provided to heat said storage portion, said storage portion being elevated to said set temperature and over by heating of said electric heater, and said amount of stored $SO_x$ being estimated on the basis of said heating pattern by said electric heater, and when the oxygen concentration in the exhaust gas being lowered, said storage portion releasing the stored $NO_x$ and reducing the released $NO_x$ by using of reduction materials in the exhaust gas, so that the temperature of said storage portion elevates by heat produced in the reduction of $NO_x$, if necessary, said amount of stored $SO_x$ being estimated on the basis of an increase value of temperature of said storage portion measured by said temperature sensor after the oxygen concentration in the exhaust gas is lowered, and the integrated amount of $SO_x$ passing through the exhaust passage during the given period or the value on the basis of said integrated amount being detected.

9. A detector for detecting sulfur components according to claim 4 wherein when the oxygen concentration in the exhaust gas being lowered, said storage portion releasing the stored $NO_x$ and reducing the released $NO_x$ by using of reduction materials in the exhaust gas, so that the temperature of said storage portion elevates by heat produced in the reduction of $NO_x$, if necessary, said amount of stored $SO_x$ being estimated on the basis of an increase value of temperature of said storage portion measured by said temperature sensor after the oxygen concentration in the exhaust gas is lowered, and the integrated amount of $SO_x$ passing through the exhaust passage during the given period or the value on the basis of said integrated amount being detected.

* * * * *